United States Patent [19]

Chiu et al.

[11] Patent Number: 5,281,276

[45] Date of Patent: Jan. 25, 1994

[54] PROCESS FOR MAKING AMYLASE RESISTANT STARCH FROM HIGH AMYLOSE STARCH

[75] Inventors: Chung-Wai Chiu, Westfield; Matthew Henley, Somerset; Paul Altieri, Belle Mead, all of N.J.

[73] Assignee: National Starch and Chemical Investment Holding Corporation, Wilmington, Del.

[21] Appl. No.: 857,530

[22] Filed: Mar. 25, 1992

[51] Int. Cl.$^5$ ............... C08B 30/00; A23L 1/05
[52] U.S. Cl. .................... 127/65; 127/32; 127/67; 127/69; 127/71; 426/661
[58] Field of Search ............. 127/65, 67, 69, 71, 127/32; 426/661

[56] References Cited

U.S. PATENT DOCUMENTS

| | | | |
|---|---|---|---|
| 3,407,070 | 10/1968 | Murray et al. | 426/661 |
| 3,556,942 | 1/1971 | Hathaway | 127/65 |
| 3,729,380 | 4/1973 | Sugimoto et al. | 195/31 R |
| 3,734,760 | 5/1973 | Hijiya et al. | 106/210 |
| 4,121,974 | 10/1978 | Hofreiter et al. | 435/275 |
| 4,971,723 | 11/1990 | Chiu | 252/315.3 |
| 5,035,930 | 7/1991 | Lacourse et al. | 428/35.6 |
| 5,051,271 | 9/1991 | Iyengar et al. | 426/658 |
| 5,169,662 | 12/1992 | Spicer | 126/449 |
| 5,176,936 | 1/1993 | Creighton et al. | 426/618 |

FOREIGN PATENT DOCUMENTS

| | | |
|---|---|---|
| WO90/15247 | 12/1990 | PCT Int'l Appl. ......... C12P 19/14 |
| WO93/03629 | 3/1993 | PCT Int'l Appl. . |
| 1313421 | 4/1970 | United Kingdom . |

OTHER PUBLICATIONS

Resistant Starch: Formation and Measurement of Starch that Survives Exhaustive Digestions with Amylolytic Enzymes During the Determination of Dietary Fiber, C. S. Berry, Journal of Cereal Science 4(4), pp. 301-314 (1986).

Ca. Inst. Food Sci. Technol. J. vol.17, No. 2 pp. 65-70, 1984 *Textural and Microstructural Changes in Corn Starch as a Function of Extrusion Variables*, J. Owusu-Ansah, et al.

Cereal Chemistry, vol. 52, May-Jun. 1975, No. 3, part 1, pp. 283-297 *Modification of Carbohydrate Components by Extrusion-Cooking of Cereal Products*, C. Mercier, et al.

Cereal Chem. 65(2):138-143, *Relationship Between Amylose Content and Extrusion-Expansion Properties of Corn Starches*, R. Chinnaswamy, et al. (1988).

Journal of Food Science, vol. 48, (1983), *Changes in Starch Fraction During Extrusion-Cooking of Corn*, M. H. Gomez, et al.

Cereal Chemistry, vol. 61, No. 6, 1984, *Extrusion Cooking and Drum Drying of Wheat Starch. I. Physical and Macromolecular Modifications*, P. Colonna, et al.

Lecture presented at the 27th Starch Convention of the Arbeitsgemeinschaft Getreideforschung in Germany from Apr. 28 to 30, 1976, *Effect of Extrusion-Cooking on Potato Starch Using a Twin Screw French Extruder*, C. Mercier.

Cereal Sci. Today, Sep. 1973, vol. 18, No. 9, p. 286, *Changes in Various Starches by Cooking-Extrusion Processing: II Physical Structure of Extruded Products*.

Journal of Food Science, vol. 58, No. 6, 1992, *Raw-Starch Degrading Amylase(s) Affect Enzyme-Resistant Starch*, pp. 1443-1444, L. Gruchala, et al.

Cereal Foods World, May 1989, vol. 34, No. 5, *Microstructural, Physicochemical, and Macromolecular Changes in Extrusion-Cooked and Retrograded Corn Starch*, R. Chinnaswamy, et al.

*Primary Examiner*—R. Bruce Breneman
*Assistant Examiner*—Patricia L. Hailey
*Attorney, Agent, or Firm*—Jane E. Gennaro

[57] ABSTRACT

A process to increase the amount of resistant starch in a starch product to at least about 15% resistant starch using a high amylose starch, such as HYLON V or HYLON VII, as the starting starch, consists essentially of the steps of gelatinizing a starch slurry, enzymatically debranching the starch, and isolating the starch product by extrusion or drying. A further increase is obtained by the addition of an inorganic salt to the debranched starch before isolation.

20 Claims, No Drawings

PROCESS FOR MAKING AMYLASE RESISTANT STARCH FROM HIGH AMYLOSE STARCH

BACKGROUND OF THE INVENTION

This invention relates to a process for the manufacture of a starch product containing at least about 15% amylase resistant starch from a starch that contains at least 40% amylose.

Starch, a complex carbohydrate, is composed of two types of polysaccharide molecules: amylose, a mostly linear and flexible polymer of D-anhydroglucose units that are linked by alpha-1,4-D-glucosidic bonds, and amylopectin, a branched polymer of amylose chains that are linked by alpha-1,6-D-glucosidic bonds. Starch is digested predominantly in the small intestine by the enzyme alpha-amylase. Alpha-amylase hydrolyzes alpha-1,4-glycosidic bonds, and therefore hydrolyzes the amylose fraction of starch almost completely to simple sugars. Alpha-amylase does not hydrolyze the alpha-1,6-D-glucosidic linkages, resulting in less complete hydrolysis of the amylopectin fraction.

It is known that certain starch processing operations result in the transformation of starch into starch that is resistant to amylase, known simply as resistant starch. Resistant starch is not digested by amylases in the small intestine, but passes into the large intestine where, research literature indicates, it behaves with properties similar to soluble and insoluble dietary fiber. Resistant starch, thus, has reduced caloric value because it resists digestion, and it is likely to be a factor in the prevention of diverticulosis and colon cancer and lowering blood cholesterol levels.

It is generally believed that resistant starch is formed when the amylose fraction of starch is retrograded or recrystallized after the gelatinization of starch. The theory is that the flexible linear amylose molecules align themselves after gelatinization into tight linear configurations that can form helices or spheres making many of the alpha-1,4-glucosidic linkages inaccessible to alpha-amylase. Normally, as described in the literature, the process for the formation of resistant starch by retrogradation is cumbersome involving the initial gelatinization and then the cooling of starch, frequently with repeated cycles.

U.S. Pat. No. 5,051,271 issued on Sep. 24 1991 to Iyengar, et al. discloses a process for preparing a food grade, insoluble bulking agent from starch involving a retrogradation followed by enzymatic or chemical hydrolysis. To prepare the insoluble bulking agent the starting starch first is dispersed in an aqueous medium and then subjected to extended incubation at temperatures down to 4° C. This step is stated to transform the starch structure to double-helical crystalline regions interspersed with amorphous regions. The reference states that since the retrogradation of amylose is retarded by the presence of amylopectin in the starch, the process can be accelerated by enzymatic conversion of amylopectin to amylose prior to retrogradation by the use of debranching enzymes, such as pullulanase or isoamylase, or by partial hydrolysis with alpha-amylase. The retrograded starch is then subjected to enzymatic or acid hydrolysis to eliminate the amorphous regions and to produce a starch that is essentially free of amorphous regions and that contains at least 90% crystalline material.

This and other reported methods for preparing resistant starch call for cycles of heating and cooling, or isolation of the resistant starch by removing non-resistant materials through enzyme or chemical hydrolysis. These methods are tedious and commercially impracticable and the need remains for a commercially feasible process.

SUMMARY OF THE INVENTION

This method for preparing a starch product containing amylase resistant starch consists essentially of the steps of gelatinizing a slurry of a starch that contains amylose in an amount greater than 40%, treating the gelatinized starch with a debranching enzyme for sufficient time to effect essentially complete debranching, deactivating the enzyme, and isolating the starch product by drying, extrusion, or crystallization by the addition of salt. The method does not require repeated cycles of gelatinization and incubation at low temperatures to produce the resistant starch product.

DETAILED DESCRIPTION OF THE INVENTION

The starches used in preparing amylase resistant starch may be derived from any source, for example, from corn, potato, sweet potato, wheat, rice, sago, tapioca, waxy maize, and sorghum. However, to obtain the high yields of this process, the preferred starting starch is a starch containing greater than 40% amylose, for example, HYLON V, a corn starch containing about 50% amylose, or HYLON VII, a corn starch containing about 70% amylose, both products of National Starch and Chemical Company, Bridgewater, N.J. The starch may be defatted or chemically modified, for example, converted, derivatized, or crosslinked, and still yield resistant starch.

The starting starch is dispersed into an aqueous slurry having a solids content of 5%–40%, preferably about 15%, and heated at sufficient temperature and pressure to effect gelatinization. Although gelatinization may be effected by any of the methods known in the art, the preferred method is to force the starch slurry through a jet cooker. Jet-cookers are well known in the industry and consist of a cooking chamber in which the starch slurry is contacted with live steam under elevated temperatures. Generally, the conditions for gelatinization are temperatures from 120°–175° C. (250° F. –350° F.), and pressures from 1.05–10.5 kg/cm$^2$ (15–150 psi). Complete gelatinization is desired and is determined visually by the total disintegration of granular structure. The gelatinization process disrupts, in whole or in part, the associative bonding of the starch molecules within the raw starch granule. This prepares the starch molecules for debranching by making them more accessible to the debranching enzyme, resulting in more uniformly debranched starch molecules.

After the starch has been gelatinized, it is then prepared for enzymatic debranching. The starch solids content is adjusted to the highest feasible solids level (to keep the amount of water low and to facilitate subsequent drying of the starch), the preferred solids content being about 15%. A higher solids starch system may be employed if the starch is processed with adequate mixing to uniformly blend enzyme and starch at the higher solids.

After the solids content is fixed, the temperature and pH of the starch dispersion are readjusted to provide optimum enzyme activity. These parameters will vary depending upon the type and source of enzyme used, the enzyme concentration, the substrate concentration, and the presence or absence of inhibitors.

The preferred enzyme for the enzymatic debranching of this process is pullulanase (E.C. 3.2.1.41; pullulan 6-glucanohydrolase), a heat stable enzyme obtained from a species of Bacillus. Pullulanase will catalyze the hydrolysis of the alpha-1,6 linkages in pullulan and amylopectin, provided that there are at least two glucose units in the side chain. However, other endo-alpha-1,6-glucanohydrolases, such as isoamylase (E.C. 3.2.1.68), or any other endo-enzyme that exhibits selectivity in cleaving the 1,6-linkages of the starch molecule, leaving the 1,4-linkages substantially intact, may be used to debranch starch according to this method.

When the enzyme used in the Bacillus pullulanase, and the starch solids content is in the range of 5%–35%, the reaction may be carried out in a pH range from 3.0–7.5, preferably from 4.5–5.5, and most preferred at 5.0. Buffers, such as acetates, phosphates, citrates, or the salts of other weak acids can be added to ensure that the pH will be at the optimum level throughout the debranching. At pH 5.0 the preferred temperature for the aqueous starch dispersion during the enzymatic debranching by the Bacillus pullulanase will be between 25°–75° C., the more preferred being between 50°–65° C., and the most preferred being 60° C. If shorter treatment times are desired, the optimum temperature range can be increased to 60°–65° C. (or higher, if the debranching enzyme is thermally stable at the higher temperatures), or a higher enzyme concentration can be used. As with other parameters of the enzyme reaction, the preferred and optimum temperature ranges will vary with changes in other parameters that affect enzyme activity, such as substrate concentration and pH, and these can be determined by the practitioner.

Optimum concentrations of enzyme and substrate are governed by the level of enzyme activity, which will vary depending upon the enzyme source, the enzyme supplier, and the concentration of the enzyme provided in commercially available batches. In general, the pullulanase enzyme is effective at 1500 PUN (pullulanlase units novo/kg starch) using a HYLON V or VII starch substrate at 15% solids content. Although the process of this invention makes use of an enzyme in solution, an enzyme immobilized on a solid support is intended to fall within the scope of this invention.

The enzymatic treatment is permitted to continue until essentially complete debranching has occurred. In most systems under optimum enzymatic conditions, complete debranching will have occurred by 48 hours. If desired, the progress of the debranching may be measured by any method known in the art for measuring the degree of enzymatic debranching of starch molecules.

After complete starch debranching has been accomplished, the enzyme is deactivated. Bacillus Pullulanase, for example, is rapidly deactivated at temperatures above about 70° C. (158° F.); therefore, the reaction using pullulanase may be conveniently terminated by increasing the temperature of the starch dispersion to at least 75° C. for about 15 minutes. Alternatively, the enzyme can be deactivated by adjusting the pH of the starch dispersion to below 3.0 and holding at that pH for about ½ hour.

If the end-use application requires purification of the starch product, the reaction impurities and by-products may be removed by dialysis, filtration, ion exchange processes, centrifugation or any other method known in the art for purifying the starch.

After debranching and deactivation of the enzyme, the starch is isolated by dehydrating or drying. It is not necessary to cool the starch to low temperatures or to store it for prolonged times to produce the resistant starch. In a preferred embodiment, the method of dehydrating is by extrusion. The dehydrating can be done to a partial extent, for example, to 60%–80% solids, and the resultant product then dried further. Alternatively, the extrusion process can be used to accomplish drying up to 100% solids. As shown in Example 4, extrusion yields higher levels of resistant starch over the drying methods. It is thought that the increased temperature and pressure imposed on the starch molecules in the extruder contributes to the association and uniform alignment of the linear starch molecules, thus increasing the amount of resistant starch.

The extrusion apparatus can be any screw-type extruder, although the twin-screw extruder is preferred. A twin-screw extruder will typically have rotating screws in a horizontal cylindrical barrel with an entry port mounted over one end and a shaping die mounted at the discharge end. When twin screws are used, they may be co-rotating and intermeshing or non-intermeshing. Each screw will comprise a helical flight or threaded section and typically will have a relatively deep feed section followed by a tapered transition section and a comparatively shallow constant-depth meter section. The screws, which are motor driven, generally fit snuggly into the cylinder or barrel to allow mixing, heating and shearing of the material as it passes through the extruder.

Control of the temperature along the length of the extruder barrel is important and is controlled in zones along the length of the screw. The heat exchange means can be, for example, a channel, chamber or bore located in the barrel wall for circulating a heated medium, such as oil, or an electrical calrod or coil. Heat exchange means may also be placed in or along the shaft of the screw device. the starch is extruded at temperatures between 60°–180° C., preferably between 110°–180° C. Variations in any of the elements used in the extruder may be made as desired in accordance with conventional design practices in the field.

Spray drying, flash drying, air drying, freeze drying, vacuum drying, belt drying, and drum drying, or any other method known and used in the art for drying starch, may also be used to dry the starch product. In general, there is no disadvantage to the more rigorous methods of drying compared to air drying. Suitable parameters for the methods of spray drying and flash drying are disclosed in the examples.

In another embodiment, the starch product is isolated by adding an inorganic salt to the starch dispersion and incubating the mixture at 50°–100° C. The salt can be any known salt that will not interfere with starch retrogradation and that will act to help draw out the water of gelatinization, permitting the association of the linear starch molecules and the formation of amylase resistant starch. Suitable salts are sodium sulfate, ammonium sulfate or magnesium sulfate, and sodium chloride, preferably are the sulfate salts, and are added to the deactivated starch slurry in a minimum of 10% of the solids content, preferably from 25%–50%. The starch is collected, washed, and dried, and contains a minimum of about 15% resistant starch.

In addition, any of the embodiments of this process can be followed by acid or enzyme hydrolysis to remove from the starch product that portion of the starch that is not resistant starch and to give a starch product containing even higher levels of resistant starch.

The following examples will more fully illustrate the preferred embodiments of this invention.

EXAMPLE 1

Prosky Method for Determining Dietary Fiber in Foods According to Prosky, et al., *J. Assoc. Off. Anal. Chem.*, 68, 677 (1985)

Reagents:

(a) Ethanol 95% v/v, technical grade.

(b) Ethanol 78%. Place 207 ml H$_2$O into 1 L volume flask. Dilute to volume with 95% EtOH. Mix and dilute to volume again with 95% EtOH if necessary. Mix (c) Acetone, reagent grade.

(d) Phosphate buffer, 0.05M, pH 6.0. Dissolve 0.875 g Na phosphate dibasic, anhydride (Na$_2$HPO$_4$) (or 1.097 g dihydrate) and 6.05 g Na phosphate monobasic monohydrate (NaH$_2$PO$_4$) (or 6.84 g dihydrate) in a ca 700 ml H$_2$O. Dilute to 1 L with H$_2$O. Check pH with pH meter.

(e) Termamyl (heat stable α-amylase) solution—No. 120 L, Novo Laboratories, Inc., Wilton Conn. 06897. Keep refrigerated.

(f) Protease. No. P-5380, Sigma Chemical Company. Keep refrigerated.

(g) Amyloglucosidase. No. A-9268, Sigma Chemical Company. Keep refrigerated.

Alternatively, a kit containing all 3 enzymes (pretested) is available from Sigma Chemical Company, Catalog No. KR-185.

(h) Sodium hydroxide solution, 0.171N. Dissolve 6.84 g NaOH ACS in ca 700 ml H$_2$O in 1 L. volume flask. Dilute to volume with H$_2$O.

(i) Phosphoric acid solution, 0.205M. Dissolve 23.64 g H$_3$PO$_4$ ACS (85%) in H$_2$O in 1 L volume flask. Dilute to volume with H$_2$O.

(j) Celite C-211, acid-washed. Fisher Scientific Company.

Method: Run blank through entire procedure along with samples to measure any contribution from reagents to residue.

Homogenize sample and dry overnight in 70° C. vacuum oven, cool in desiccator, and dry-mill portion of sample to 0.3-0.5 mm mesh.

Weigh duplicate 1 g samples, accurate to 0.1 mg, into 400 ml, tall-form beakers. Sample weights should not differ by >20 mg. Add 50 ml pH 6.0 phosphate buffer to each beaker. Check pH and adjust if necessary. Add 0.1 ml Termanyl solution. Cover beaker with Aluminum foil and place in boiling H$_2$O bath 15 minutes. Shake gently at 5 minute intervals. Increase incubation time when number of beakers in boiling H$_2$O bath makes it difficult for beaker contents to reach internal temperature of 100° C. Use thermometer to ascertain that 100° is attained at 15 minutes. Total of 30 minutes in H$_2$O bath should be sufficient.

Cool solutions to room temperature. Adjust to pH 7.5±0.1 by adding 10 ml 0.171N NaOH solution.

Add 5 mg protease. (Protease sticks to spatula, so it may be preferable to prepare enzyme solution just before use with ca 0.1 ml phosphate buffer and pipet required amount).

Cover beaker with aluminum foil. Incubate 30 minutes at 60° C. with continuous agitation. Cool. Add 10 ml 0.205M H$_3$PO$_4$ solution to adjust pH to 4.5±0.2. Add 0.3 ml amyloglucosidase, cover with aluminum foil and incubate 30 minutes at 60° C. (Measure volume before heating.) Let precipitate form at room temperature for 60 minutes.

Weigh crucible containing Celite to nearest 0.1 mg, then wet and redistribute bed of Celite in crucible by using stream of 78% EtOH from wash bottle. Apply suction to draw Celite onto fritted glass as even mat. Maintain suction and quantitatively transfer precipitate from enzyme digest to crucible.

Wash residue successively with three 20 ml portions of 78% EtOH, two 10 ml portions of 95% EtOH, and two 10 ml portions of acetone. Gum may form with some samples, trapping liquid. If so, break surface film with spatula to improve filtration. Time for filtration and washing will vary from 0.1-6 hours, averaging 1.2 hour per sample. Long filtration times can be avoided by careful intermittent suction throughout filtration.

Dry crucible containing residue overnight in 70° C. vacuum oven or 105° C. air oven. Cool in desiccator and weigh to nearest 0.1 mg. Subtract crucible and Celite weight to determine weight of residue.

Analyze residue from sample of set of duplicates for protein and ash. Subtract protein and ash values from residue to obtain TDF.

Determination of blank:

$$\text{blank} = \text{mg blank residue} - \frac{(\% \text{ protein in blank} + \% \text{ ash in blank}) \times \text{mg blank residue}}{100}$$

Determination of TDF (%):

$$TDF \% = \frac{\text{mg residue} - [(\% \text{ protein in residue} + \% \text{ ash in residue}) \times \text{mg residue}] - \text{blank}}{\text{mg sample (wt)}} \times 100$$

Example 2

Method for production of resistant starch (RS) using debranching enzyme

The base starch is slurried into water and jet cooked at temperatures between 149°–160° C. (300°–320° F.). The starch is then placed into a constant temperature bath set at 60° C. and sodium benzoate (approximately 0.1% by weight of the starch) is added to the cooked starch to preserve freshness. The starch dispersion is diluted to a solids range of 5% 14 40%, preferably 10% –20%. (Variations of solids content within this range were found experimentally not to be significant.) The pH is adjusted to within 4.5-5.5, preferably 5.0, with a solution of 3:1 water/concentrated HCl. Promozyme 200 L, a commercial preparation of pullulanase, a product of NOVO-NORDISK, Danbury Conn., is added when the starch temperature is about 60° C. (140° F.). The enzyme is allowed to debranch the starch for 48 hours and then is deactivated by lowering the pH to 2.7-3.0 with a solution of 3:1 water/concentrated HCl for ½ hour. The starch is neutralized to a pH of 5.0-5.5 with 3% NaOH in water. The debranched starch is then filtered through a Buchner funnel. The insoluble fraction is resuspended in water and isolated by one of the drying techniques described in the following examples.

EXAMPLE 3

Effect of Debranching on Resistant Starch Levels in HYLON VII Sample

This example shows that the yield of resistant starch is increased when the starch is debranched after gelatinization.

A. HYLON VII starch (2 kg) was slurried into water (11.31 kg) and jet cooked at 149°–158° C. (300°–315° F.). The starch was placed into a constant temperature bath set at 60° C. and sodium benzoate (2 g) was added to the cooked starch to preserve freshness. The dispersed starch was adjusted to pH 5.0 with a solution of 3:1 water/concentrated HCl. Promozyme 200 L (140 ml) was added when the starch temperature reached 60° C. (140° F.). The enzyme was allowed to debranch the starch for 48 hours and then was deactivated by lowering the pH to 2.7–3.0 with a solution of 3:1 water/concentrated HCl for ½ hour. The starch was neutralized to a pH of 5.0–5.5 with 3% NaOH in water. The insoluble fraction was spray dried without a filtration step using an Anhydro portable spray dryer (lab type, S1, Anhydro Corp., Copenhagen, Denmark) having an inlet temperature of 210°–215° C., and outlet temperature of 90°–100° C. A two fluid atomizing nozzle with air pressure at 2.10 kg/cm$^2$ (30 psi) was used to atomize the starch. The starch product was found to possess 27.5% RS when assayed by the Prosky method.

B. HYLON VII starch (2 kg) was slurried at 10% solids and jet cooked at approximately 158°–160° C. (315° F.). The hot dispersion was allowed to cool to room temperature while being well agitated. Agitation was continued for about 24 hours at room temperature. Part of the starch was removed for extrusion drying (see Example 4-A) and the remainder was spray dried according to the method of Example 3-A. The resulting starch product, which was not debranched, had a value of 9.4% RS by the Prosky method.

EXAMPLE 4

Effect of Extrusion Drying on Resistant Starch Levels in HYLON VII Sample

This example shows that the yield of resistant starch is increased when the starch product is dried by extrusion.

A. The suspension of retrograded but not debranched HYLON VII from sample 3-B (having 9.4% RS) was extruded using the conditions of sample 4-C. The extrudate was air dried further and ground to a fine powder. It was analyzed for resistant starch by the Prosky method and the RS level was found to increase to 14.3% RS. This sample shows that the extrusion process itself increases the level of RS, whether or not the sample is debranched.

B. HYLON VII starch (2 kg) was slurried into water (11.31 kg) and jet cooked at 149°–158° C. (300°–315° F.). The starch was placed into a constant temperature bath set at 60° C. and sodium benzoate (2 g) was added to the cooked starch to preserve freshness. The dispersed starch was adjusted to pH 5.0 with a solution of 3:1 water/concentrated HCl. Promozyme 200L (140 ml) was added when the starch temperature reached 60° C. (140° F.). The enzyme was allowed to debranch the starch for 48 hours and then was deactivated by lowering the pH to 2.7–3.0 with a solution of 3:1 water/concentrated HCl for ½ hour. The starch was neutralized to a pH of 5.0–5.5 with 3% NaOH in water. The sample was divided into two parts, and one part was spray dried according to the method in Example 3-A. This part was assayed for resistant starch by the Prosky method and yielded 21.5% RS.

C. The remaining part of the sample was extruded on a Warner & Pfleiderer Type ZSK-30 twin-screw extruder. The screw configuration used is designated 12–44 and was used with a 5 mm (×2) die. The screws were operated at a speed of 400–450 rpm and the barrel heating zones were set to 60°/100°/120°/150°/150° C. The barrel was placed under a vacuum of 35–40 cm Hg (14–16 inches Hg) through a single barrel vent. The extruded starch rope was air dried and ground to a fine powder. The sample was found to contain 30.0% RS, by the Prosky method.

The results of this Example are set out in Table 1 and show that the combination of debranching and extrusion drying gives the highest yields of RS.

TABLE 1

| Effects of Debranching and Extrusion Drying on Yields of RS | | | |
|---|---|---|---|
| Sample | Debranched | Extruded | % RS |
| 3-B | no | no | 9.4 |
| 4-A | no | yes | 14.3 |
| 4-B | yes | no | 21.5 |
| 4-C | yes | yes | 30.0 |

EXAMPLE 5

Effect of alpha-Amylase on Resistant Starch Formation.

This example illustrates that only a debranching reaction is suitable for preparing high levels of RS and that, in fact, the addition of alpha-1,4 specific enzymes to a starch dispersion before retrogradation may be detrimental to the formation of RS.

HYLON VII starch (2 kg) was slurried into water (11.31 kg) and jet cooked at 149°–158° C. (300°–315° F.). The starch was placed into a constant temperature bath set at 80° C. and sodium benzoate (2 g) was added to the cooked starch to preserve freshness. The dispersed starch was adjusted to pH 6.0 with a solution of 3:1 water/concentrated HCl. The batch was split evenly into two portions and each batch maintained at 80° C. Bacterial alpha-amylase (BAN 120 L, a product of Novo-Nordisk, Danbury Conn.) was added at levels of 0.005% and 0.01%, based on the weight of starch, to the two fractions, respectively. The first fraction (sample 5-A) was degraded to a viscosity of 100 mPas (cps) (at 10% solids, 21.5° C.) and the second (sample 5-B) to a viscosity of 30–50 mPas (cps) (at 10% solids, 21.5° C.). The alpha-amylase was then deactivated by adding 3:1 water/concentrated HCl until the dispersion was adjusted to pH 3.0 and held for ½ hour. The temperature of the starch was lowered to 60° C. and the pH adjusted to 5.0. The debranching enzyme, pullulanase, Promozyme (65 ml), was added to each fraction and allowed to react for 48 hours. The pullulanase was deactivated according to the method of Example 2 and the insolubles isolated by filtration. The insoluble product was collected by resuspending the insoluble fraction in water and spray drying according to the method of Example 3-A. The two products were analyzed for resistant starch by the Prosky method and were found to contain 17.5% and 1.8% RS respectively.

EXAMPLE 6

Debranching of Amylose to Increase the Yield of Resistant Starch.

This example illustrates the use of debranching enzyme to prepare resistant starch from amylose. The increase in resistant starch from isolated amylose shows that both amylose and amylopectin, not just the amylopectin, must be debranched to prepare a starch product with high levels of resistant starch.

A. Potato amylose was isolated using the following procedure: Potato starch (100 parts, d.b.) and sodium sulfite (1 part) were added to 1300 parts of a 10% solution of magnesium sulfate (130 parts anhydrous magnesium sulfate in 1170 parts water). The pH was adjusted to 7.5 with 25% $H_2SO_4$. The slurry was then passed through a thermal converter with a pump pressure of 7.03 $kg/cm^2$ (100 psi), pump speed of 7.56 liters per min (2 gal/min), temperature of 158° C. (315° F.), with 1 minute dwell time, and the highest possible steam input (>90%). After cooking the percent solids were determined to be 14.1% (corresponding to 8.0% $MgSO_4$ and 6.0% potato starch). (At this point, the salt concentration should be within 8.0%–9.5%, and if not in this range can be brought to this concentration by either dilution with water or addition of $MgSO_4$.) The solution was cooled to 20° C. and allowed to age for 20 hours while being slowly agitated. After aging, the amylose was recovered by centrifuging and washed by repeated suspension in water followed by centrifuging. The product was then air dried and analyzed for RS by the Prosky method. The product was found to contain 21.9% RS.

B. A portion of the isolated amylose (200 g) (from part A, above) was dispersed at 10% solids and jet cooked at about 155° C. (310° F.). The cooked amylose was allowed to cool to room temperature with good agitation. It was then held at room temperature for 20 hours to allow the amylose to retrograde. The amylose is collected as a dry powder by spray drying according to the method of Example 3-A. The product was analyzed for RS by the Prosky method and found to contain 26.4% RS.

C. A portion of the isolated amylose (250 g) (from part A, above) was dispersed at 15% solids and was jet cooked at about 155° C. (310° C.). It was debranched with 18.75 ml Promozyme following the procedure outlined in Example 2. The reaction was allowed to proceed for 24 hours, after which the enzyme was deactivated with acid. The sample was recovered by spray drying according to the method of Example 3A, analyzed for RS by the Prosky method and found to contain 50.3% RS.

The results are set out in Table 2.

TABLE 2

Effect on Resistant Starch Levels of Gelatinization and Debranching on 100% Amylose Base

| Sample | Treatment | % RS |
|---|---|---|
| 6-A | none | 21.9 |
| 6-B | gelatinization and retrogradation | 26.4 |
| 6-C | gelatinization, debranching and retrogradation | 50.3 |

EXAMPLE 7

Effect of Amylose Level in Starch Base on Resistant Starch Production.

This example shows that the yield of resistant starch increases as the amount of amylose in the base starch increases.

All of the samples were gelatinized and debranched according to the procedure outlined in Example 2 from the base starches and in the amounts and enzyme concentrations as follows:

A. Waxy corn starch (0% amylose) (1000 g) was used as the base. Promozyme (75 ml) was used to debranch the starch. The product was collected as a dry powder in 100% yield by spray drying; no filtration step was used. The powder was found to contain 0% resistant starch when assayed by the Prosky method.

B. Corn starch (25% amylose) (500 g) was used as the base. Promozyme (37 ml) was used to debranch the starch. The product was collected as a dry powder in 100% yield by spray drying; no filtration step was used. The powder was found to contain 0% resistant starch when assayed by the Prosky method.

C. HYLON V, a high amylose corn starch (about 50% amylose), (500 g) was used as the base. Promozyme (35 ml) was used to debranch the starch. The product was collected as a dry powder in 100% yield by spray drying; no filtration step was used. The product was found to contain 14.3% resistant starch when assayed by the Prosky method.

D. HYLON VII, a high amylose corn starch (about 70% amylose), (500 g) was used as the base. Promozyme (37 ml) was used to debranch the starch. The product was collected as a dry powder in 100% yield by spray drying; no filtration step was used. The powder was found to contain 28.8% resistant starch when assayed by the Prosky method.

The results are set out in Table 3.

TABLE 3

Effect of Amylose Content on Yields of Resistant Starch

| Sample | % Amylose | % RS Yield |
|---|---|---|
| 7-A | 0 | 0 |
| 7-B | 25 | 0 |
| 7-C | 50 | 14.3 |
| 7-D | 70 | 28.8 |
| 6-C | 100 | 50.3 |

EXAMPLE 8

Comparison of Drying Methods. This example shows that efficient high temperature drying may be used to recover the starch product containing resistant starch.

The starch product was prepared according to the method of Example 2 except that the starch used was 10 kg of HYLON VII; the debranching reaction was carried out using 750 ml Promozyme; and the starch was dispersed at 11% solids. The insoluble product was isolated by centrifugation using a perforated bowl centrifuge with a linen cloth as the filter medium. The cake obtained from the centrifuge was divided into two fractions.

A. One fraction was re-slurried and spray dried using the method and conditions of Example 3-A. The dry powder obtained was analyzed by the Prosky method and found to contain 25% resistant starch.

B. The other portion was flash dried using a laboratory flash dryer having an inlet temperature of 250° C. (480° F.) and an outlet temperature of 175° C. (350° F.) at a feed rate of 7.0 g/min. The dry powder obtained from this process was analyzed by the Prosky method and was found to contain 30.6% resistant starch.

C. A sample was prepared according to the procedure in Example 2 except that the starch used was 3 kg of HYLON VII starch and the conversion was carried out for 72 hours. The insoluble product obtained by filtration was crumbled, spread thinly and allowed to dry under ambient conditions. The dry particles were recovered and ground to a fine powder. The powder was analyzed by the Prosky method and was found to contain 26.0% resistant starch.

The results are set out in Table 4.

TABLE 4

| Effect of Method of Drying on RS Production | | | |
|---|---|---|---|
| Sample | Method | Drying Temp. °C. | % RS |
| 8-A | Spray | 260 | 25.0 |
| 8-B | Flash | 250 | 30.6 |
| 8-C | Air | 25 | 26.0 |

EXAMPLE 9

Production of Resistant Starch from Chemically Modified Starches

This example shows that defatting or chemical modification does not inhibit resistant starch formation.

A. Control. A control was prepared in the same way as Example 3.

B. Acid converted starch. The product was prepared according to the method described in Example 2 except that National 78-0150 (1 kg), a thin-boiling high amylose starch, available from National Starch and Chemical Company, Bridgewater, N.J., at 17% starch solids, was debranched with 75 ml of Promozyme. After enzyme deactivation, the product was spray dried according to the method of Example 3-A. The RS level was found to be 20.8% by the Prosky method.

C. Esterified starch. HYLON VII starch was modified with 1.25% octenyl succinic anhydride under the following conditions: HYLON VII (800 g) was slurried into 1200 ml of water. The pH of the slurry was raised to 7.4 with 3% NaOH. While maintaining the pH at 7.3–7.4, three increments of octenyl succinic acid anhydride, 3.3 ml each, were added with agitation ½ hour apart. When the reaction no longer consumed caustic, it was determined to be complete and the starch was collected by filtration.

This esterified starch was then used as the base for preparing the starch product containing resistant starch. The product was prepared according to the method described in Example 2 except that the reaction was carried out at 15% solids, the pH of the dispersion was 5.3, 37.50 ml of Promozyme was used, and no filtration step was employed. The reaction mix was spray dried, as is, following the enzyme deactivation step and the spray dried powder was found to possess 22.0% RS by the Prosky method.

D. Defatted starch. Granular HYLON VII was defatted by repeated extraction with methanol using a Soxeleht extractor for ten days. A portion of this defatted starch (500 g) was then debranched according to the method of Example 2, except that the sample was not filtered. A second portion was retrograded without debranching according to the method described in Example 3-B. Both products were isolated as powders by spray drying and were analyzed by the Prosky method.

The results are set out in Table 5.

TABLE 5

| Production of Resistant Starch from Debranched Chemically Modified Starch | | |
|---|---|---|
| Sample | Modification | % RS |
| 3-B (control) | None | 9.4 |
| 9-A | Debranched | 25.0 |
| 9-B | Acid Converted/Debranched | 20.8 |
| 9-C | Esterified/Debranched | 22.0 |
| 9-D | Defatted/Debranched | 32.4 |

EXAMPLE 10

Production of a Purified Resistant Starch Product

Debranched HYLON VII was prepared according to the method of Example 2 except that the product was not filtered. Instead 7.5 ml of the reaction mix was placed in a boiling water bath and heated to 90° C. Termamyl 120 L, a heat stable alpha-amylase produced by NOVO-NORDISK, (7.5 ml) was added to the starch and the reaction mix incubated at 85°–90° C. for 24 hours. The insoluble product was isolated by filtration in 60% yield and was dried under ambient conditions by crumbling the filter cake and spreading it thinly on a drying rack. The dried particles were ground to a fine powder. The powder was analyzed by the Prosky method and found to contain 65% RS.

EXAMPLE 11

Production of Resistant Starch and Recovery by Salt Precipitation and Air Drying A debranched HYLON VII suspension prepared according to the method used in Example 2, prior to the filtration step, was separated into samples designated A through G. In an amount by weight of solids of the solution, food grade salts were added to the samples as indicated in Table 6, except that salt was not added to sample A. Each of these mixtures was heated to 95° C. and held at that temperature for 24 hours. The sample was cooled to about 25° C. and ethanol was added to bring the solvent to a solution of 50:50 ethanol:water and to precipitate out the starch product. The product was filtered over a Buchner funnel, washed twice with 50:50 water:ethanol and air dried. The results are set out in Table 6 and show that the amount of resistant starch is increased in a starch product obtained by salt precipitation.

TABLE 6

| Salt Induced Formation of Resistant Starch | | | |
|---|---|---|---|
| Sample | Salt | Concentration in sample | % RS |
| 11-A | — | 0 | 22.6 |
| 11-B | $(NH_4)_2SO_4$ | 25% | 40.8 |
| 11-C | $Na_2SO_4$ | 10% | 33.8 |
| 11-D | $Na_2SO_4$ | 25% | 42.1 |
| 11-E | $MgSO_4$ | 25% | 40.9 |
| 11-F | NaCl | 25% | 33.3 |
| 11-G | NaCl | 50% | 44.0 |

We claim:

1. A process to increase the amount of resistant starch in a starch product to at least about 15% resistant starch from a starting starch containing at least 40% amylose that consists essentially of the steps of:

(a) preparing an aqueous slurry of a starch that contains at least 40% amylose;
(b) gelatinizing the starch slurry;
(c) adding an effective amount of a debranching enzyme to the gelatinized starch to hydrolyze the 1,6-glucosidic bonds of the starch molecules;
(d) isolating the debranched resistant starch product by drying or extrusion.

2. The process according to claim 1 in which the starch in step (a) contains about 70% amylose.

3. The process according to claim 1 in which the starch in step (a) is potato amylose.

4. The process according to claim 1 in which the starch in step (a) is a defatted starch or a chemically modified starch.

5. The process according to claim 1 in which the debranching enzyme is selected from the group consisting of pullulanase and isoamylase.

6. A process to increase the amount of resistant starch in a starch product to at least about 15% resistant starch that consists essentially of the steps of:
(a) preparing an aqueous slurry of a starch containing at least 40% amylose;
(b) gelatinizing the starch slurry;
(c) adding an effective amount of a debranching enzyme to the gelatinized starch to hydrolyze the 1,6-glucosidic bonds of the starch molecules;
(d) adding an inorganic salt to the debranched starch to a final concentration of at least about 10% by weight of total solids;
(e) incubating the starch and salt mixture at temperatures between 50°-100° C.;
(f) cooling the starch and salt mixture to about 25° C. and adding ethanol to facilitate precipitation of the starch product;
(g) isolating the precipitated resistant starch product by drying or extrusion.

7. The process according to claim 6 in which the starch in step (a) contains about 70% amylose.

8. The process according to claim 6 in which the starch in step (a) is potato amylose.

9. The process according to claim 6 in which the starch in step (a) is a defatted starch or a chemically modified starch.

10. The process according to claim 6 in which the debranching enzyme is selected from the group consisting of pullulanase and isoamylase.

11. The process according to claim 6 in which the inorganic salt is added to the debranched starch in an amount of 10%-50% by weight of the starch solids.

12. The process according to claim 6 in which the inorganic salts are selected from the group consisting of ammonium sulfate, sodium sulfate, magnesium sulfate, and sodium chloride.

13. A resistant starch product containing at least about 15% resistant starch made by the process that consists essentially of the steps of:
(a) preparing an aqueous slurry of a starch containing at least 40% amylose;
(b) gelatinizing the starch slurry;
(c) adding an effective amount of a debranching enzyme to the gelatinized starch to hydrolyze the 1,6-glucosidic bonds of the starch molecules;
(d) adding an inorganic salt to the debranched starch to a final concentration of at least about 10% by weight of total solids;
(e) incubating the starch and salt mixture at temperatures between 50°-100° C.;
(f) cooling the starch and salt mixture to about 25° C. and adding ethanol to facilitate precipitation of the starch product;
(g) isolating the precipitated resistant starch product by extrusion or drying.

14. A process to increase the amount of resistant starch in a starch product to at least about 15% resistant starch from a starch containing at least 40% amylose that consists essentially of the steps of:
(a) preparing an aqueous slurry of a starch that contains at least 40% amylose;
(b) gelatinizing the starch slurry;
(c) adding an effective amount of a debranching enzyme to the gelatinized starch to hydrolyze the 1,6-glucosidic bonds of the starch molecules;
(d) treating the debranched starch by acid or enzyme hydrolysis to remove that portion of the starch that is not resistant starch; and
(e) isolating the resistant starch product by extrusion or drying.

15. A process to increase the amount of resistant starch in a starch product to at least about 15% resistant starch from a starch containing at least 40% amylose that consists essentially of the steps of:
(a) preparing an aqueous slurry of a starch that contains at least 40% amylose;
(b) gelatinizing the starch slurry;
(c) retrograding the gelatinized starch;
(d) extruding the retrograded starch at temperatures between 60°-180° C. to obtain the resistant starch product.

16. The process according to claim 15 in which the starch in step (a) is potato amylose.

17. The process according to claim 15 in which the resistant starch product is treated by acid or enzyme hydrolysis to remove that portion of the starch that is not resistant starch before extruding the retrograded starch.

18. A resistant starch product containing at least about 15% resistant starch made by the process according to claim 15.

19. A process to increase the amount of resistant starch in a starch product to at least about 15% resistant starch that consists essentially of the steps of:
(a) preparing an aqueous slurry of a starch containing at least 40% amylose;
(b) gelatinizing the starch slurry;
(c) adding an effective amount of a debranching enzyme to the gelatinized starch to hydrolyze the 1,6-glucosidic bonds of the starch molecules;
(d) adding an inorganic salt to the debranched starch to a final concentration of at least about 10% by weight of total solids;
(e) incubating the starch and salt mixture at temperatures between 50°-100° C.;
(f) cooling the starch and salt mixture to about 25° C. and adding ethanol to facilitate precipitation of the starch product;
(g) treating the debranched starch by acid or enzyme hydrolysis to remove that portion of the starch that is not resistant starch; and
(h) isolating the precipitated resistant starch product by extrusion or drying.

20. A resistant starch product containing at least about 15% resistant starch made by the process according to claim 19.

* * * * *